(12) United States Patent
Markle

(10) Patent No.: US 6,677,170 B1
(45) Date of Patent: Jan. 13, 2004

(54) METHOD FOR DETERMINING PROCESS LAYER THICKNESS USING SCATTEROMETRY MEASUREMENTS

(75) Inventor: Richard J. Markle, Austin, TX (US)

(73) Assignee: Advanced Micro Devices, Inc., Austin, TX (US)

(*) Notice: Subject to any disclaimer, the term of this patent is extended or adjusted under 35 U.S.C. 154(b) by 257 days.

(21) Appl. No.: 09/863,596

(22) Filed: May 23, 2001

(51) Int. Cl.$^7$ .................. H01L 21/66; G01R 31/26
(52) U.S. Cl. ............................ 438/16; 716/4
(58) Field of Search ........................ 438/16, 17–18, 438/14–15, 5–13, 800; 716/4–18; 356/357, 355, 359, 360, 381, 382

(56) References Cited

U.S. PATENT DOCUMENTS

| | | | |
|---|---|---|---|
| 4,999,014 A | * | 3/1991 | Gold et al. |
| 5,555,472 A | * | 9/1996 | Clapis et al. ............... 356/504 |
| 6,051,348 A | | 4/2000 | Marinaro et al. ............ 430/30 |
| 6,245,584 B1 | | 6/2001 | Marinaro et al. ............ 438/14 |
| 6,433,878 B1 | | 8/2002 | Niu et al. .................... 356/603 |
| 2002/0135781 A1 | | 9/2002 | Singh et al. ................. 356/601 |

OTHER PUBLICATIONS

International Sematech "Advanced Process Control Framework Initiative (APCFI) Project: Overview" Tech Transfer #99053735A–TR. Jun. 30, 1999 <<http://www.sematech.org/public/docubase/document/3736atr.pdf>> viewed Aug. 21, 2003.*

* cited by examiner

Primary Examiner—Craig Thompson
(74) Attorney, Agent, or Firm—Williams, Morgan & Amerson, P.C.

(57) ABSTRACT

A method for determining thickness of a process layer includes providing a wafer having a grating structure and a process layer formed over the grating structure; illuminating at least a portion of the process layer and the grating structure with a light source; measuring light reflected from the illuminated portion of the grating structure and the process layer to generate a reflection profile; and determining a thickness of the process layer based on the reflection profile. A processing line includes a metrology tool having a light source, a detector, and a data processing unit. The metrology tool is adapted to receive a wafer having a grating structure and a process layer formed over the grating structure. The light source is adapted to illuminate at least a portion of the process layer and the grating structure. The detector is adapted to measure light reflected from the illuminated portion of the grating structure and the process layer to generate a reflection profile. The data processing unit is adapted to determine a thickness of the process layer based on the generated reflection profile.

28 Claims, 6 Drawing Sheets

METHOD FOR DETERMINING PROCESS LAYER THICKNESS USING SCATTEROMETRY MEASUREMENTS

BACKGROUND OF THE INVENTION

1. Field of the Invention

This invention relates generally to the field of semiconductor device manufacturing and, more particularly, to a method and apparatus for determining process layer thickness using scatterometry measurements.

2. Description of the Related Art

A conventional integrated circuit device, such as a microprocessor, is typically comprised of many thousands of semiconductor devices, e.g., transistors, formed above the surface of a semi-conductive substrate. For the integrated circuit device to function, the transistors must be electrically connected to one another through conductive interconnect structures. Many modern integrated circuit devices are very densely packed, i.e., there is very little space between the transistors formed above the substrate. Thus, these conductive interconnect structures must be made in multiple layers to conserve plot space on the semiconductive substrate.

The conductive interconnect structures are typically accomplished through the formation of a plurality of conductive lines and conductive plugs, commonly referred to as contacts or vias, formed in alternative layers of dielectric materials formed on the device. As is readily apparent to those skilled in the art, the conductive plugs are means by which various layers of conductive lines, and/or semiconductor devices, may be electrically coupled to one another. The conductive lines that connect the various interconnect structures are commonly formed in trenches defined in the dielectric layers.

A contact is generally used to define an interconnect structure (e.g., comprising polysilicon or metal) to an underlying polysilicon layer (e.g., source/drain or gate region of a transistor), while a via denotes a metal to metal interconnect structure. For contacts and vias, a contact opening is formed in an insulating layer overlying the conductive member. A second conductive layer is then formed over the contact opening and electrical communication is established with the conductive member.

An exemplary semiconductor device 100 is shown in FIG. 1. The semiconductor device 100 includes trenches 110, 120 used to form conductive line interconnect structures and a contact opening 130 used to form a conductive plug interconnect structure defined in a base insulating layer 135. The contact opening 130 communicates with an underlying conductive feature 137 (e.g., polysilicon line) formed in a previous layer of the semiconductor device 100. Prior to filling the trenches 110, 120 and contact opening 130 with a conductive metal (e.g., by electroplating a copper fill layer), the trenches 110, 120 and contact opening 130 are lined with one or more barrier layers 140 and/or seed layers 150. A stop layer 160 is provided for protecting the base insulating layer 135 during a subsequent polishing process used to remove portions of the layers 140, 150 and copper fill layer extending beyond the trenches 110, 120 and contact opening 130. The barrier layer 140 functions to inhibit electromigration in the copper fill layer. Electromigration is the displacement of metal ions in the copper layer due to the current flow in the line. The force of the propagating electrons is commonly referred to as "electron wind." Over long periods of time, voids left behind by displaced ions accumulate. Eventually, an open circuit may occur, causing the semiconductor device to irreparably fail. Commonly used barrier layer materials include tantalum and tantalum nitride. An exemplary barrier layer 140 configuration includes a tantalum nitride layer lining the trenches 110 and contact opening 120 and a tantalum layer overlying the tantalum nitride layer.

The seed layer 150, typically comprising a deposited layer of copper or a copper alloy, is formed over the barrier layer 140 by a physical vapor deposition process (i.e., sputtering). The seed layer 150 is coupled to a voltage source during the subsequent plating of the copper layer to fill the trenches 110, 120 and contact opening 130 to complete the interconnect structures.

Controlling the thicknesses of the barrier and/or seed layers 140, 150 is important for controlling the performance of the completed devices. If the barrier layer 140 has insufficient thickness the protection provided against electromigration is compromised. If the seed layer 150 thickness is not sufficient, the subsequent plating process will leave gaps or voids in the interconnect structure compromising its integrity. If the barrier and/or seed layers 140, 150 are too thick, the aspect ratio of the structure may be increased to a point where the plating process is ineffective and voids or seams form in the copper fill material.

The present invention is directed to overcoming, or at least reducing the effects of, one or more of the problems set forth above.

SUMMARY OF THE INVENTION

One aspect of the present invention is seen in a method for determining thickness of a process layer. The method includes providing a wafer having a grating structure and a process layer formed over the grating structure; illuminating at least a portion of the process layer and the grating structure with a light source; measuring light reflected from the illuminated portion of the grating structure and the process layer to generate a reflection profile; and determining a thickness of the process layer based on the reflection profile.

Another aspect of the present invention is seen in a processing line including a metrology tool. The metrology tool includes a light source, a detector, and a data processing unit. The metrology tool is adapted to receive a wafer having a grating structure and a process layer formed over the grating structure. The light source is adapted to illuminate at least a portion of the process layer and the grating structure. The detector is adapted to measure light reflected from the illuminated portion of the grating structure and the process layer to generate a reflection profile. The data processing unit is adapted to determine a thickness of the process layer based on the generated reflection profile.

BRIEF DESCRIPTION OF THE DRAWINGS

The invention may be understood by reference to the following description taken in conjunction with the accompanying drawings, in which like reference numerals identify like elements, and in which.

Figure 1:
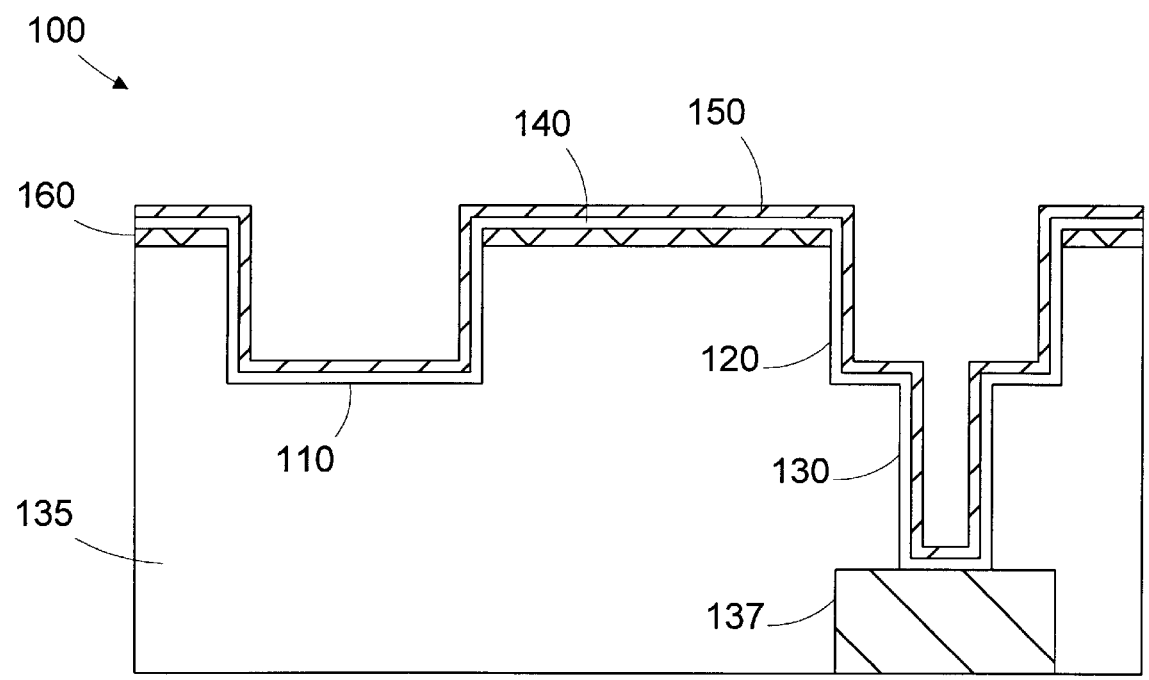
FIG. 1 is a cross section view of an exemplary semiconductor device on which a process layer is deposited over a grating structure.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Figure 2:
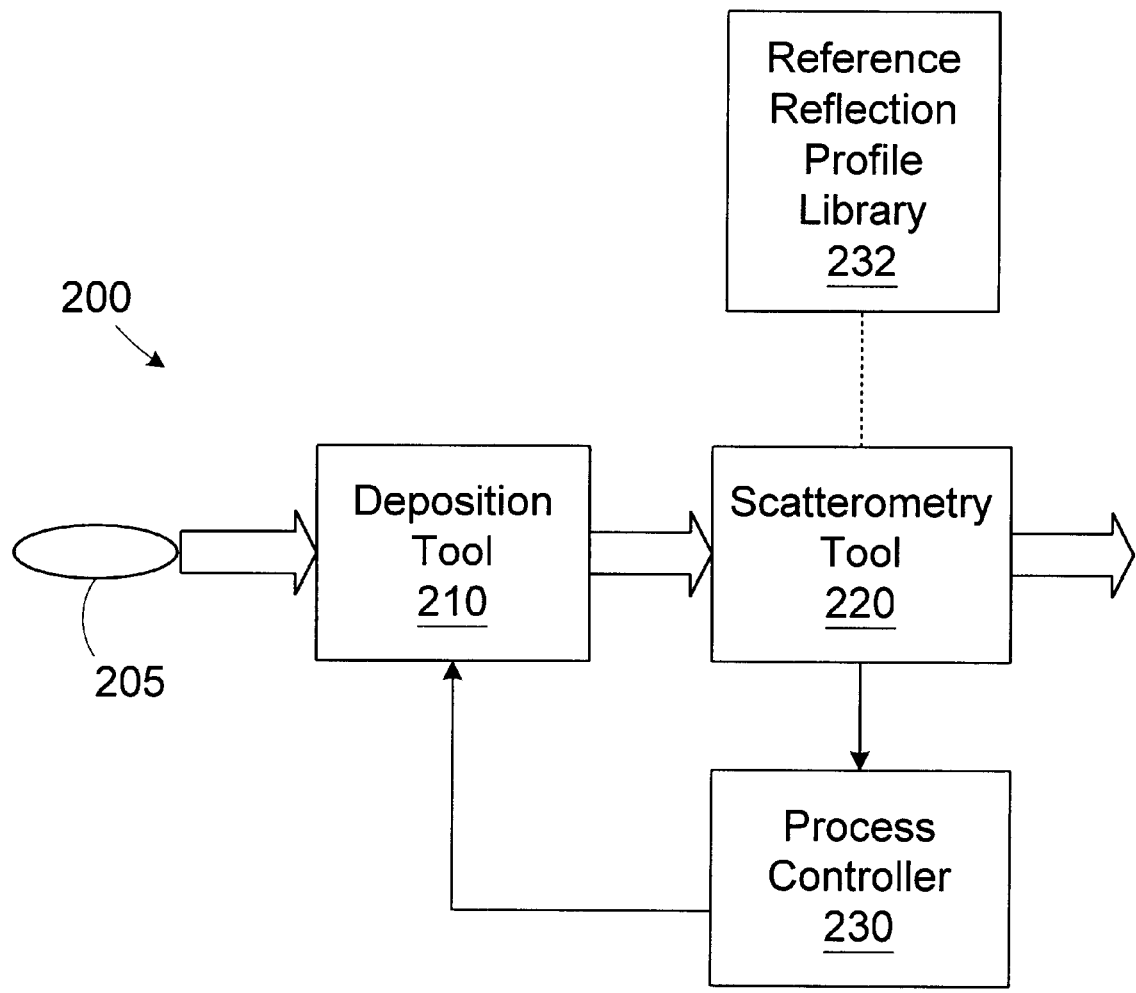
FIG. 2 is a simplified diagram of an illustrative processing line for processing wafers in accordance with one illustrative embodiment of the present invention.

Referring to FIG. 2, a simplified diagram of an illustrative processing line 200 for processing wafers 205 in accordance with one illustrative embodiment of the present invention is provided. The processing line 200 includes a deposition tool 210 for depositing a process layer (not shown in FIG. 2) on the wafer 205. In the illustrated embodiment, the process layer may be a barrier layer or a seed layer (e.g., tantalum, tantalum nitride, copper, copper alloy, etc.) that is formed over a grating structure (e.g., interconnect trenches and/or contact openings). Particular techniques for depositing process layers of various composition are well known to those of ordinary skill in the art. An exemplary tool suitable for use as the deposition tool 210 is a physical vapor deposition (PVD) tool, such as an Endura offered by Applied Materials, Inc. of Santa Clara, Calif. Variations in the deposition operations of the deposition tool 210 and the geometry of the features that form the grating structure may cause variations in the thickness of the process layer deposited.

The processing line 200 includes a scatterometry tool 220 adapted to measure thickness of the process layer formed on the wafer 205. In general, the scatterometry tool 220 includes optical hardware, such as an ellipsometer or reflectometer, and a data processing unit loaded with a scatterometry software application for processing data collected by the optical hardware. For example, the optical hardware may include a model OP5230 or OP5240 with a spectroscopic ellipsometer offered by Therma-Wave, Inc. of Freemont Calif. The data processing unit may comprise a profile application server manufactured by Timbre Technologies, a fully owned subsidiary of Tokyo Electron Limited, Inc. of Tokyo, Japan and distributed by Therma-Wave, Inc.

The scatterometry tool 220 may be external to the deposition tool 210 or, alternatively, the scatterometry tool 220 may be installed in an in-situ arrangement. A process controller 230 is provided for controlling the operations of the deposition tool 210 based on the measured thickness of the deposited process layer.

Although the invention is described as it may be implemented for determining the thickness of a barrier layer or seed layer over an interconnect feature, its application is not so limited, as it may be applied to the formation of many types of process layers over various types of grating structures.

The process controller 230 may provide feedback information to the deposition tool 210 and adjust its operating recipe to control the thickness of the deposition process for the current wafer being processed or for subsequently processed wafers 205. These feedback and feedforward control techniques will be described in greater detail below.

In the illustrated embodiment, the process controller 230 is a computer programmed with software to implement the functions described. However, as will be appreciated by those of ordinary skill in the art, a hardware controller designed to implement the particular functions may also be used. Moreover, the functions performed by the process controller 230, as described herein, may be performed by multiple controller devices distributed throughout a system. Additionally, the process controller 230 may be a stand-alone controller, it may be integrated into a tool, such as the deposition tool 210 or the scatterometry tool 220, or it may be part of a system controlling operations in an integrated circuit manufacturing facility.

Portions of the invention and corresponding detailed description are presented in terms of software, or algorithms and symbolic representations of operations on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" or "displaying" or the like, refer to the action and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

An exemplary software system capable of being adapted to perform the functions of the process controller 230, as described, is the Catalyst system offered by KLA-Tencor, Inc. The Catalyst system uses Semiconductor Equipment and Materials International (SEMI) Computer Integrated Manufacturing (CIM) Framework compliant system technologies and is based on the Advanced Process Control (APC) Framework. CIM (SEMI E81-0699—Provisional Specification for CIM Framework Domain Architecture) and APC (SEMI E93-0999—Provisional Specification for CIM Framework Advanced Process Control Component) specifications are publicly available from SEMI.

In one embodiment, the scatterometry tool 220 measures thickness of the process layer as found on features formed in the production devices. For example, the scatterometry tool 220 may measure the thickness of a barrier or seed layer deposited in a trench or contact opening used to form an actual interconnect feature. In some cases, the geometry of the features or the presence of underlying structures may inhibit scatterometry measurements. Accordingly, test structures having the same general configuration as features (e.g., trenches) formed on the wafer 205 may be employed. The test structures may be formed in a region of the wafer 205 not normally used for forming devices (e.g., in the periphery region where identification codes are typically scribed or in the scribe lines between production die).

Figure 3:
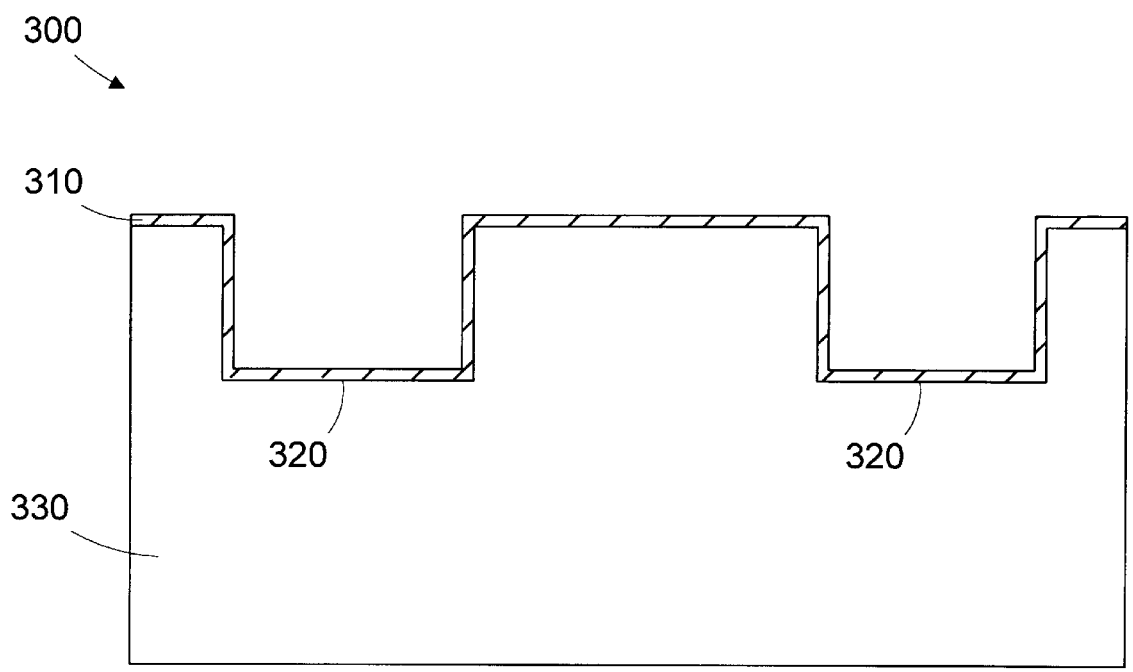
FIG. 3 is a cross section view of an exemplary semiconductor device including a test structure.

Referring briefly to FIG. 3, an exemplary grating structure 300 that may used as a test structure on the wafer 205 is shown. A process layer 310 is formed over the grating structure 300. In the illustrated embodiment, the grating structure 300 includes trenches 320 formed in a base layer 330 (e.g., a dielectric layer). In one illustrative embodiment, the grating structure 300 has the same general construction (e.g., geometry, materials, pitch, etc.) as features included in the production devices formed on the wafer 205.

Figure 4:
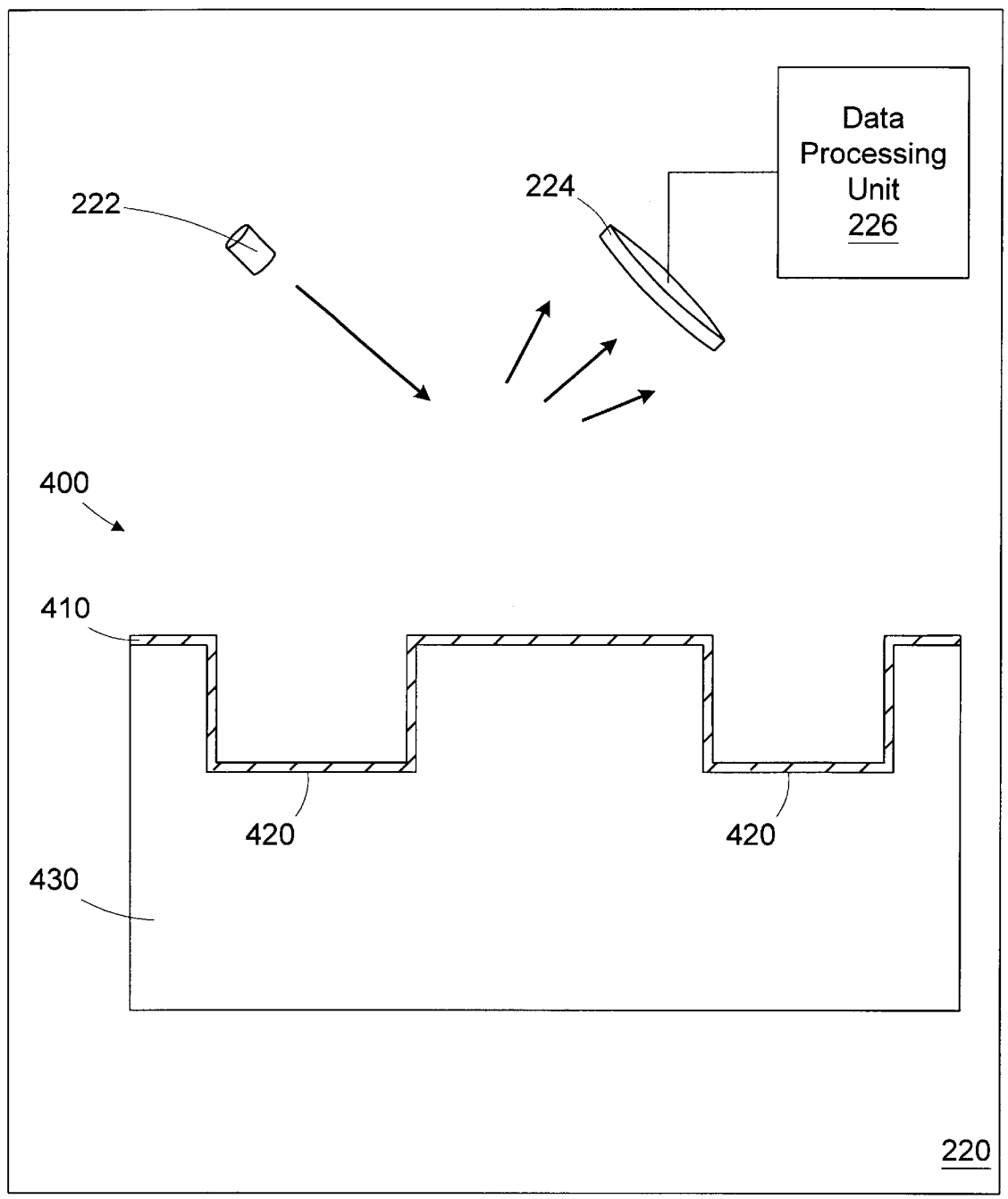
FIG. 4 is a simplified view of the scatterometry tool of FIG. 2 loaded with a wafer including a grating structure.

Turning now to FIG. 4, a simplified view of the scatterometry tool 220 loaded with a wafer 205 having a grating structure 400 and a process layer 410 overlying the grating structure 400 is provided. The grating structure 400 may be a feature formed in a production device on the wafer 205 (i.e., as shown in FIG. 1), or alternatively, the grating structure 400 may be a test structure similar to the grating structure 300 discussed above in reference to FIG. 3. In the illustrated embodiment, the grating structure 400 includes trenches 420 defined in a base layer 430. The scatterometry tool 220, includes a light source 222 and a detector 224 positioned proximate the grating structure 400 and process layer 410. The light source 222 of the scatterometry tool 220 illuminates at least a portion of the process layer 410 and the grating structure 400, and the detector 224 takes optical measurements, such as intensity or phase, of the reflected light. A data processing unit 225 receives the optical measurements from the detector 224 and processes the data to determine the thickness of the process layer 410.

The scatterometry tool 220 may use monochromatic light, white light, or some other wavelength or combinations of wavelengths, depending on the specific implementation. The angle of incidence of the light may also vary, depending on the specific implementation. The light analyzed by the scatterometry tool 220 typically includes a reflected component (i.e., incident angle equals reflected angle) and a refracted component (i.e., incident angle does not equal the reflected angle). For purposes of discussion here, the term "reflected" light is meant to encompass both components. In an application where the process performed by the deposition tool 210 produces interference with the scatterometry signal (e.g., in plasma enhanced CVD tool), a filtering process may be employed to remove such interference prior to analyses by the scatterometry tool 220.

Variations in the thickness of the process layer 410 causes changes in the reflection profile (e.g., intensity vs. wavelength—tan($\delta$), phase vs. wavelength—sin($\Psi$), where $\delta$ and $\Psi$ are common scatterometry outputs known to those of ordinary skill in the art) measured by the scatterometry tool 220 as compared to the light scattering profile that would be present in a process layer 410 having an acceptable thickness.

Figure 5A:
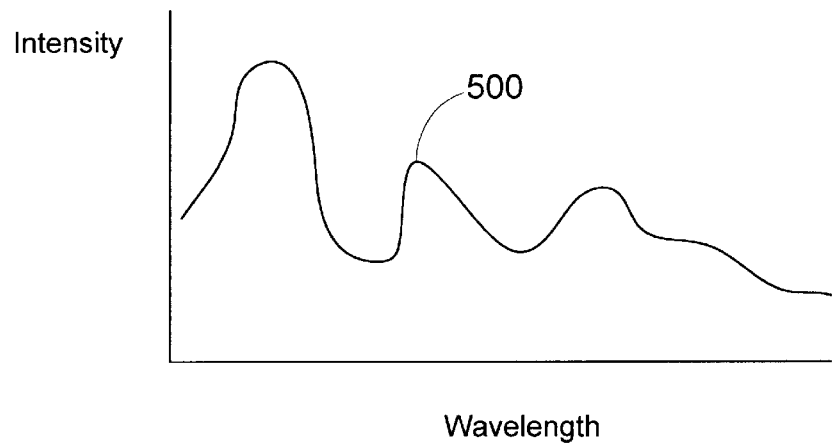
FIGS. 5A, 5B, and 5C illustrate a library of exemplary scatterometry curves used to characterize the wafer measured in the scatterometry tool of FIG. 4.
Figure 5B:
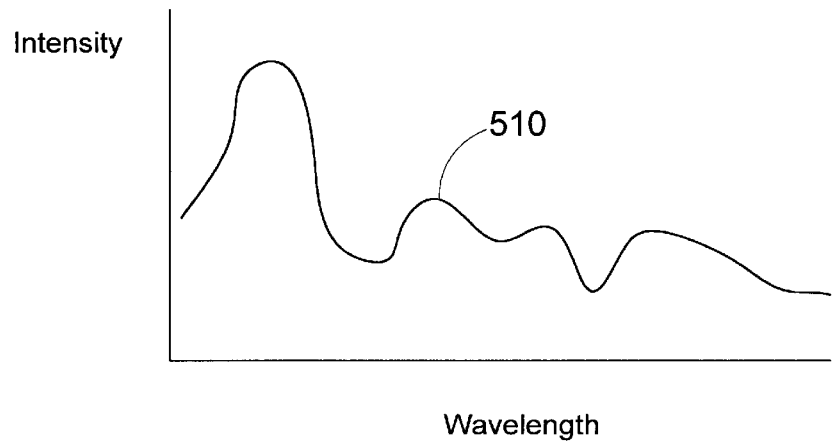
Figure 5C:
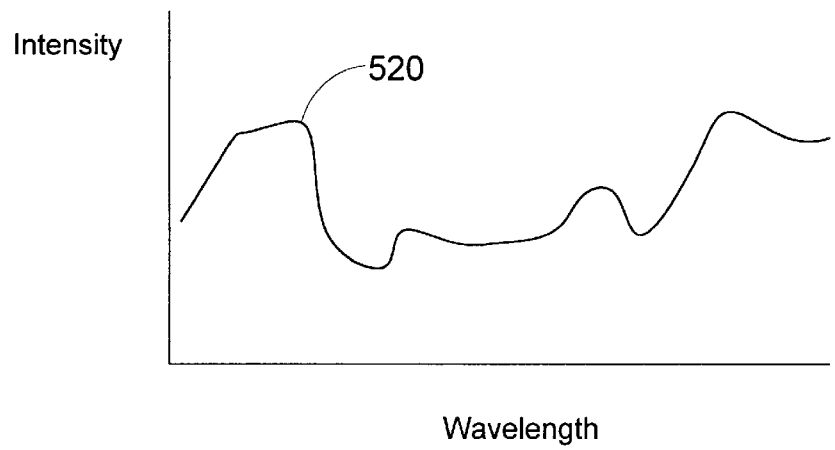

FIGS. 5A, 5B, and 5C illustrate exemplary reflection profiles 500, 510, 520 that may be included in a reference reflection profile library 232 (see FIG. 2) used by the data processing unit 225 to characterize the thickness of the process layer 410 based on the measured reflection profiles. The particular reflection profile expected for any structure depends on the specific geometry of the grating structure 400, the thickness of the process layer 410, and the parameters of the measurement technique employed by the scatterometry tool 220 (e.g., light bandwidth, angle of incidence, etc.). The profiles in the reference reflection profile library 232 are typically calculated theoretically by employing Maxwell's equations to model individual spectra based on the expected characteristics of the process layer 410 and the topology and geometry of the grating structure 400. Spectra are generated at a pre-determined resolution for every profile that may be expected, and the sum of all said spectra constitute the reference reflection profile library 232. Scatterometry libraries are commercially available from Timbre Technologies, Inc. The profiles in the reference reflection profile library 232 may also be generated empirically by measuring reflection profiles of sample wafers and subsequently characterizing the measured wafers by destructive or non-destructive examination techniques.

The reflection profile 500 of FIG. 5A represents an expected profile for a process layer 410 with a desired thickness for the process layer 410. The reflection profile 510 of FIG. 5B represents an expected profile for a process layer 410 that has a reduced thickness as compared to the desired thickness, and reflection profile 520 of FIG. 5C represents an expected profile for a process layer 410 that has an increased thickness as compared to the desired thickness. The reflection profiles of process layers 410 with varying thickness values may be included in the reference reflection profile library 232.

The data processing unit 225 compares the measured reflection profile to the reference reflection profile library 232. Each reference profile has an associated thickness metric. The data processing unit 225 determines the reference reflection profile having the closest match to the measured reflection profile. Techniques for matching the measured reflection profile to the closest reference reflection profile are well known to those of ordinary skill in the art, so they are not described in greater detail herein.

In another embodiment, the process controller 230 or other external controller (not shown) may be adapted to compare the measured reflection profile to the reference reflection profile library 232. In such a case, the scatterometry tool 220 would output the matching reference reflection profile, and the process controller 230 may link that reference reflection profile to an associated thickness metric.

In another embodiment, the measured reflection profile may be compared to a target reflection profile selected from the reference reflection profile library 232 for a process layer 410 having a known and desired thickness (e.g., the profile 500 of FIG. 5A). For example, a target reflection profile may be calculated for a process layer 410 having an ideal or acceptable thickness using Maxwell's equations, and that target reflection profile may be stored in the reference reflection profile library 232. Thereafter, the measured reflection profile of a process layer 410 having an unknown thickness is compared to the target reflection profile. Based upon this comparison, a relatively rough approximation of the thickness may be determined. That is, by comparing the measured reflection profile to the target reflection profile, the thickness of the process layer 410 may be approximated, such that further matching of the measured reflection profile with additional reference reflection profiles from the reference reflection profile library 232 is unwarranted. Using this technique, an initial determination may be made as to the thickness of the process layer 410. Of course, this step may be performed in addition to the matching or correlating of a measured reflection profile to a reference reflection profile from the reference reflection profile library 232 as described above.

After receiving the thickness metric from the scatterometry tool 220, the process controller 230 may take a variety of autonomous actions. In one embodiment of the present invention, the process controller 230 is adapted to modify the operating recipe of the deposition tool 210 based on the thickness metric to control deposition operations on subsequent wafers processed by the deposition tool 210.

Various operating recipe parameters of the deposition tool 210 may be controlled to affect the thickness of the deposited process layer 410. For example, commonly known recipe parameters that affect thickness are deposition time, temperature, reactive gas flow rates, pressure, etc.

The process controller 230 may also control the operation of the deposition tool 210 in real time to terminate the deposition process when a target thickness for the process layer 410 is reached. The scatterometry tool 220 periodically generates a measured reflection profile and compares it to a target reflection profile. Particular techniques for determining the "fit" between the target reflection profile and the measured reflection profile are well known to those of ordinary skill in the art. One exemplary technique includes determining the mean squared distance between the target reflection profile and the measured reflection profile.

When the difference between the target reflection profile and the measured reflection profile is less than a predetermined threshold, the scatterometry tool 220 sends an endpoint signal to the deposition tool 210 to terminate the deposition process. The specific threshold employed depends on the comparison technique used and the accuracy of the scatterometric measurements. The frequency of the measurements taken by the scatterometry tool 220 may be varied as a matter of design choice. For example, during a typical deposition process, the scatterometry tool 220 may generate a reflection profile approximately every 1–3 seconds. Measurements may also be taken at different rates during the duration of the deposition process, i.e., more measurements may be taken as the process nears endpoint. The deposition process may or may not be stopped during the period when the scatterometry measurements are being taken.

The process controller 230 may use a control model of the deposition tool 210 for changing its operating recipe. For example, the process controller 230 may use a control model relating the measured thickness to a particular operating recipe parameter in the deposition tool 210 to control the deposition time, temperature, reactive gas flow rates, pressure, etc., to correct for thickness deviations. The control model may be developed empirically using commonly known linear or non-linear techniques. The control model may be a relatively simple equation based model (e.g., linear, exponential, weighted average, etc.) or a more complex model, such as a neural network model, principal component analysis (PCA) model, or a projection to latent structures (PLS) model. The specific implementation of the model may vary depending on the modeling technique selected.

A thickness model may be generated by the process controller 230, or alternatively, it may be generated by a different processing resource (not shown) and stored on the process controller 230 after being developed. The thickness model may be developed using the deposition tool 210 or using a different tool (not shown) having similar operating characteristics. For purposes of illustration, it is assumed that the thickness model is generated and updated by the process controller 230 or other processing resource based on the actual performance of the deposition tool 210 as measured by the scatterometry tool 220. The thickness model may be trained based on historical data collected from numerous processing runs of the deposition tool 210.

Figure 6:
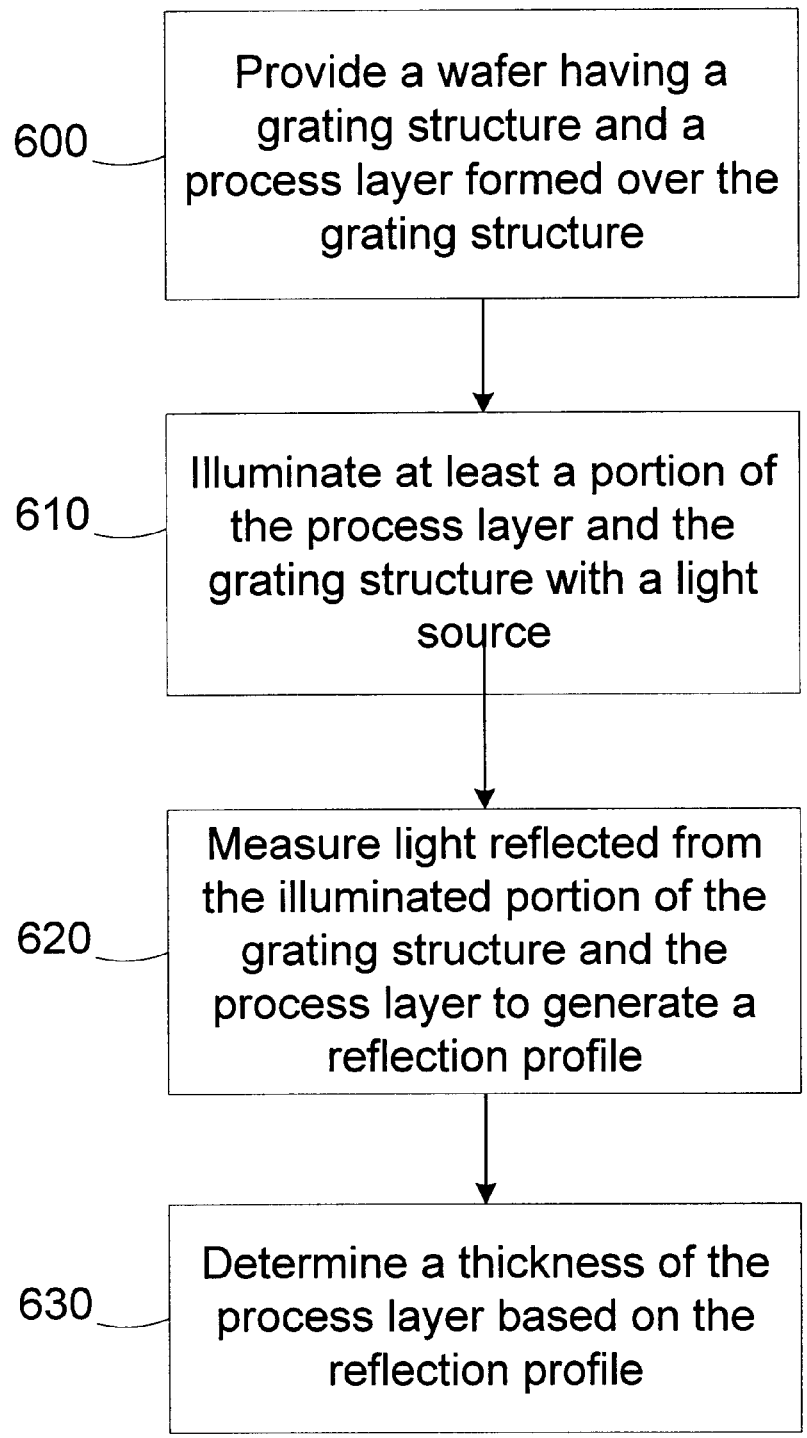
FIG. 6 is a simplified flow diagram of a method for determining process layer thickness using scatterometry measurements in accordance with another illustrative embodiment of the present invention.

Referring now to FIG. 6, a simplified flow diagram of a method for determining thickness of a process layer in accordance with another illustrative embodiment of the present invention is provided. In block 600, a wafer having a grating structure 400 and a process layer 410 formed over the grating structure 400 is provided. In block 610, at least a portion of the process layer 410 and the grating structure 400 is illuminated with a light source. In block 620, light reflected from the illuminated portion of the grating structure 400 and process layer 410 is measured to generate a reflection profile. In block 630, the thickness of the process layer 410 is determined based on the reflection profile.

Monitoring thickness based on feedback from the scatterometry tool 220, as described above, has numerous advantages. The deposition tool 210 may be controlled to decrease variability in the thickness of the process layer 410. Decreased variation increases both the quality of the devices produced on the processing line 200 and the efficiency of the processing line 200.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed:

1. A method for determining thickness of a process layer, comprising:

providing a wafer having a grating structure and a process layer formed over the grating structure;

illuminating at least a portion of the process layer and the grating structure with a light source;

measuring light reflected from the illuminated portion of the grating structure and the process layer to generate a reflection profile; and determining a thickness of the process layer based on the reflection profile.

2. The method of claim 1, wherein determining the thickness of the process layer further comprises:

comparing the generated reflection profile to a library of reference reflection profiles, each reference reflection profile having an associated thickness metric;

selecting a reference reflection profile closest to the generated reflection profile; and determining the thickness of the process layer based on the thickness metric associated with the selected reference reflection profile.

3. The method of claim 1, wherein generating the reflection profile comprises generating the reflection profile based on at least one of intensity and phase of the reflected light.

4. The method of claim 1, wherein providing the wafer comprises providing the wafer having the grating structure formed in a test structure on the wafer.

5. The method of claim 1, wherein providing the wafer comprises providing the wafer having the grating structure formed in a production device on the wafer.

6. The method of claim 1, wherein determining the thickness of the process layer further comprises:

comparing the generated reflection profile to a target reflection profile; and determining the thickness of the process layer based on the comparison of the generated reflection profile and the target reflection profile.

7. The method of claim 1, further comprising determining at least one parameter of an operating recipe of a deposition tool based on the determined thickness.

8. The method of claim 7, wherein determining the at least one parameter of the operating recipe further comprises determining at least one of a deposition time, a temperature, a reactive gas flow rate, and a pressure.

9. The method of claim 1, wherein providing the wafer further comprises forming the process layer on the wafer, the process layer overlying the grating structure, and the method further comprises:

comparing the generated reflection profile to a target reflection profile; and terminating the forming of the process layer based on the comparison of the measured reflection profile and the target reflection profile.

10. The method of claim 9, wherein terminating the forming of the process layer further comprises terminating the forming of the process layer in response to the difference between the measured reflection profile and the target reflection profile being less than a predetermined threshold.

11. The method of claim 10, wherein comparing the measured reflection profile to the target reflection profile further comprises determining a mean squared distance between the measured reflection profile and the target reflection profile.

12. The method of claim 11, wherein terminating the forming of the process layer further comprises terminating the forming of the process layer in response to the mean squared distance between the measured reflection profile and the target reflection profile being less than the predetermined threshold.

13. A method for determining thickness of a process layer, comprising:

providing a wafer having a grating structure and a process layer formed over the grating structure;

illuminating at least a portion of the process layer and the grating structure with a light source;

measuring light reflected from the illuminated portion of the grating structure and the process layer to generate a reflection profile;

comparing the generated reflection profile to a library of reference reflection profiles, each reference reflection profile having an associated thickness metric;

selecting a reference reflection profile closest to the generated reflection profile; and determining a thickness of the process layer based on the thickness metric associated with the selected reference reflection profile.

14. The method of claim 13, wherein generating the reflection profile comprises generating the reflection profile based on at least one of intensity and phase of the reflected light.

15. The method of claim 13, wherein providing the wafer comprises providing the wafer having the grating structure formed in a test structure on the wafer.

16. The method of claim 13, wherein providing the wafer comprises providing the wafer having the grating structure formed in a production device on the wafer.

17. The method of claim 13, further comprising determining at least one parameter of an operating recipe of a deposition tool based on the determined thickness.

18. The method of claim 17, wherein determining the at least one parameter of the operating recipe further comprises determining at least one of a deposition time, a temperature, a reactive gas flow rate, and a pressure.

19. A method for determining thickness of a process layer, comprising:

providing a wafer having a grating structure and a process layer formed over the grating structure;

illuminating at least a portion of the process layer and the grating structure with a light source;

measuring light reflected from the illuminated portion of the grating structure and the process layer to generate a reflection profile;

comparing the generated reflection profile to a target reflection profile; and determining a thickness of the process layer based on the comparison of the generated reflection profile and the target reflection profile.

20. The method of claim 19, wherein generating the reflection profile comprises generating the reflection profile based on at least one of intensity and phase of the reflected light.

21. The method of claim 19, wherein providing the wafer comprises providing the wafer having the grating structure formed in a test structure on the wafer.

22. The method of claim 19, wherein providing the wafer comprises providing the wafer having the grating structure formed in a production device on the wafer.

23. The method of claim 19, further comprising determining at least one parameter of an operating recipe of a deposition tool based on the determined thickness.

24. The method of claim 23, wherein determining the at least one parameter of the operating recipe further comprises determining at least one of a deposition time, a temperature, a reactive gas flow rate, and a pressure.

25. The method of claim 19, wherein providing the wafer further comprises forming the process layer on the wafer, the process layer overlying the grating structure, and the method further comprises terminating the forming of the process layer based on the comparison of the measured reflection profile and the target reflection profile.

26. The method of claim 25, wherein terminating the forming of the process layer further comprises terminal ting the forming of the process layer in response to the difference between the measured reflection profile and the target reflection profile being less than a predetermined threshold.

27. The method of claim 26, wherein comparing the measured reflection profile to the target reflection profile further comprises determining a mean squared distance between the measured reflection profile and the target reflection profile.

28. The method of claim 27, wherein terminating the forming of the process layer further comprises terminating the forming of the process layer in response to the mean squared distance between the measured reflection profile and the target reflection profile being less than the predetermined threshold.

* * * * *